United States Patent [19]

Brown et al.

[11] 4,254,765

[45] Mar. 10, 1981

[54] LIMB PROTECTIVE COVERINGS

[76] Inventors: Ronald E. Brown, 152 Ordale Blvd., Pittsburgh, Pa. 15228; Jack M. Grinwis, 142 Glenfield Dr., Pittsburgh, Pa. 15235

[21] Appl. No.: 67,338

[22] Filed: Aug. 17, 1979

[51] Int. Cl.³ .............................................. A61F 13/00
[52] U.S. Cl. ...................................... 128/82; 128/157
[58] Field of Search .......... 128/82, 157, 165, DIG. 15

[56] References Cited

U.S. PATENT DOCUMENTS

| | | | |
|---|---|---|---|
| 3,741,203 | 6/1973 | Liman | 128/82 |
| 3,747,125 | 7/1973 | Goldman et al. | 128/82 X |
| 3,789,842 | 2/1974 | Froimson | 128/DIG. 15 |
| 3,877,426 | 4/1975 | Nirschl | 128/165 |
| 4,054,952 | 10/1977 | Swallow | 128/DIG. 15 |
| 4,178,924 | 12/1979 | Baxter | 128/82 |

*Primary Examiner*—John D. Yasko
*Attorney, Agent, or Firm*—Buell, Blenko, Ziesenheim & Beck

[57] ABSTRACT

A limb protective covering is provided having a tubular sleeve of plastic and an integral hand or foot receiving member and an elongate closure strap having a panel intermediate its ends fastened to the sleeve by fastening to an inner rigidifying panel with the sleeve sandwiched between.

9 Claims, 4 Drawing Figures

LIMB PROTECTIVE COVERINGS

This invention relates to limb protective coverings and particularly to a waterproof protective covering for bandaged or injured portions of the arms and legs.

Persons who have sustained injuries to the limbs, i.e. the arms and legs must frequently wear a bandage, a cast or some form of covering or dressing for extended periods of time. During such periods of time it is necessary that the person bathe or be bathed with the attendant risk of wetting the bandage or cast. Such inadvertent wetting is frequently very undesirable and just as frequently is very difficult to avoid.

The use of a waterproof covering over such bandaged or cast limbs is of course the first thing that comes to mind and in fact the art is replete with devices designed to prevent wetting of bandages and casts during bathing. Typical of the devices heretofore proposed are those disclosed in Bellasalma U.S. Pat. No. 4,036,220, Goldman et al. U.S. Pat. No. 3,747,125, Little et al. U.S. Pat. No. 4,043,326, Cook U.S. Pat. No. 3,906,941, Guinzburg U.S. Pat. No. 2,244,871, King et al. U.S. Pat. No. 1,980,486, Liman U.S. Pat. No. 3,741,203, MacKay U.S. Pat. No. 3,735,759 and Lipson U.S. Pat. No. 3,785,374. Unfortunately, these devices are either too expensive and complex or are inadequate to do the required job. The Bellasalma patent has a flexible tubular covering member with a foam rubber ring fastened around substantially the entirety of the top edge with an excess length portion and a loop and hook fastener thereon. This type of structure is subject to two problems. First, the foam rubber ring accumulates and holds water. Second, the arrangement is such that, for a limb whose diameter is less than the diameter of the tubular member, there is a large overlap of material and of rubber ring which results in substantial leakage around the limb in that area. The sheath device of Goldman eliminates the problem mentioned above in connection with Bellasalma but has its own problems. The primary problem in Goldman resides in the fact that welding or adhesive fastening of a strap creates an area of apparent weakness in the body of the plastic sheet and it ruptures and tears readily in such area. There is the additional problem that there is no known adhesive which will attach Velcro to polyethylene and like plastics. The Little structure depends on elasticity of the top part of the cover to provide a seal. The problem is that the seal varies with the size of the limb. On large limbs, it is too tight and restricts blood flow while on small limbs it is too loose and permits leakage. The Cook device is a separate bag and tie. The problem here is obvious, the bag and tie bend to separate in use with the bag coming loose from the limb. The problem in Guinzburg is that there is no real seal but simply a pair of annular barrier rings with little or no sealing effect depending upon limb size. Lipson requires an inflatable cuff and again the seal is not reproducible from one diameter limb to another. MacKay and Liman patents provided zippered devices which are expensive and not truly waterproof.

We have invented a limb protective covering which is very inexpensive to make yet free of all of the defects of the prior art. In our invention the seal is excellent regardless of the size of the limb being covered.

We provide a limb protective covering comprising an elongate generally tubular flexible, waterproof plastic member having at one end one of a foot and hand receiving member and at the other end an opening receiving a limb to be covered, an elongate strap like closure member adapted to encircle the limb of a user at the said opening, said closure member having an intermediate panel member fixed to a minor portion of the wall of said tubular member adjacent the said opening and first and second strap members extending from opposite ends of said panel member, said first member having a rigid loop on the end remote from the panel, the second strap having mating engagement fabric strips thereon whereby the second strap may be passed through rigid loop on the first member, tightened into a water tight seal on the limb and engaged upon itself with the mating engagement fabric, a rigidifying panel corresponding generally to said intermediate panel member cooperating with said intermediate panel to support the wall portion of the tubular member to which said intermediate portion is fastened and fastening means cooperating with said rigidifying panel and intermediate panel to fix the wall portion of the tubular member thereto. Preferably plastic tubular member and hand and foot receiving member is preferably made of polyethylene. The fastening means is preferably fabric stitching passing through said intermediate member and rigidifying member with the wall portion of the tubular member sandwiched between and embracing a substantial portion of their areas. The closure member is preferably spaced from the top opening of the tubular member, however, it may be fixed close to the top of the tubular member, in which case a loop is preferably provided on the side of the tubular member opposite the intermediate panel through which said closure member is passed.

In the foregoing general description of our invention, we have set out certain objects, purposes and advantages of this invention. Other objects, purposes and advantages of this invention will be apparent from a consideration of the following description and the accompanying drawings in which.

Figure 1:
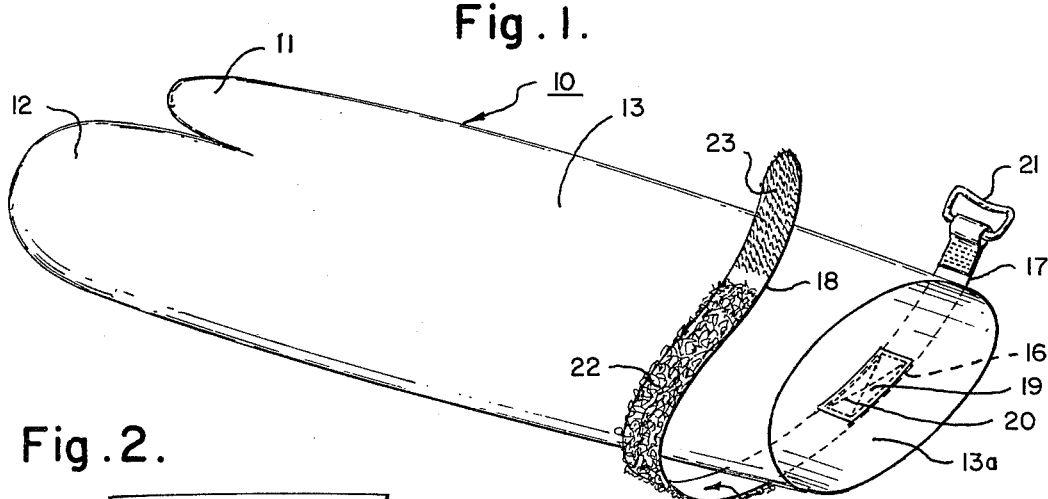
FIG. 1 is an isometric view of a hand and arm protective covering according to this invention.
Figure 2:
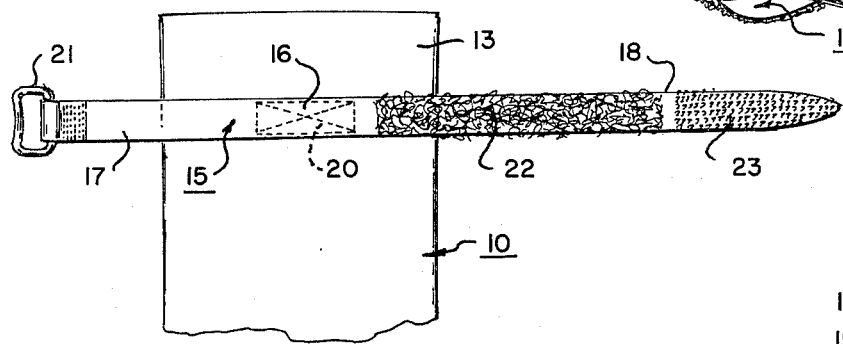
FIG. 2 is a side elevation of a lower arm and hand enclosed in the protective covering of this invention.
Figure 3:
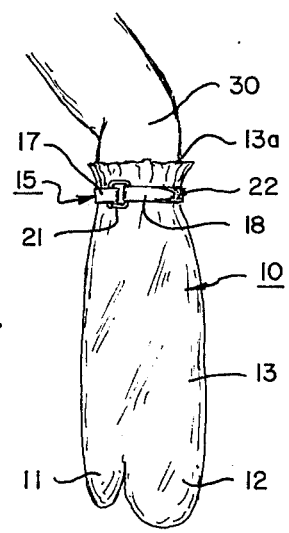
FIG. 3 is an enlarged view of the top of the protective covering of FIG. 1 showing the exterior of the closure member in detail.

Referring to the drawings we have illustrated a glove or mitten-like protective covering 10 made of polyethylene plastic and having a thumb portion 11, finger portion 12 and an elongate tubular sleeve 13. A closure member 15 is fixed to one side of the sleeve 13 through a panel 16 intermediate its strap ends 17 and 18. Panel 16 is stitched to a resin impregnated fabric rigidifying panel 19 on the opposite side of sleeve wall 13 by means of stitching 20 which passes through all three members 16, 13 and 19 over a pattern covering a substantial portion of the surface of the panel 16. One end 17 is provided with a loop 21 of metal or rigid plastic, the other end 18 is provided a strip of female engagement fabric 22 intermediate the panel 16 and the strap end and a second strip of male engagement fabric 23 at the end. Typical of such engagement fabric fasteners is that fastener sold under the name of "Velcro" fastener.

In use, the limb to be protected, e.g. an arm and hand, are inserted through the open end 13a until the thumb enters thumb cover 11 and the fingers enter mitt portion 12. End 18 is then inserted through loop 21 and drawn back upon itself, with the top of sleeve 13 tucking regularly around the arm 30 until tight. The male engagement fabric 23 is then pushed against the female fabric 22 to engage the two and hold the closure in place.

Figure 4:
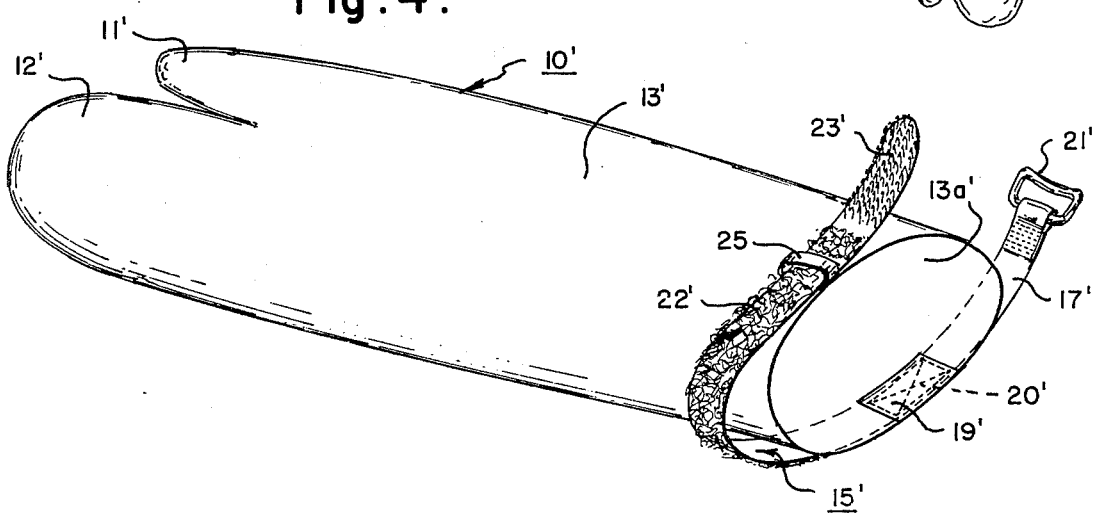
FIG. 4 is a second embodiment of the invention.

In the embodiment illustrated in FIG. 4 we have illustrated another embodiment in which those parts which are identical bear like numbers with a prime sign. Here the closure member 15' is attached close to the top of sleeve 13' and a loop 25 is attached to the side opposite rigidifying panel 19' to confine the closure member 15' to the top of sleeve 13' so that the sleeve will be retained within the closure member when tightened.

In the preferred structure described above, we have illustrated a fabric rigidifying panel 19; however, the rigidifying panel may be of any material which will attach panel 16 to sleeve 13 over sufficient area to prevent tearing of sleeve 13 while the closure 15' is being tightened. Thus, it is possible that the parts may be assembled by stitching, by use of a double-sided adhesive sheet or tape, or by any other equivalent means.

In the foregoing specification we have set out certain preferred practices and embodiments of our invention; however, it will be understood that this invention may be otherwise practiced within the scope of the following claims.

We claim:

1. A limb protective covering comprising an elongate generally tubular, flexible, waterproof plastic member having at one end one of an integral foot and hand receiving member and at the other end an opening receiving the limb to be covered, an elongate strap-like closure member adapted to encircle the limb of a user below said opening, said closure member having an intermediate panel member fixed to a minor portion of the wall of said tubular member adjacent the said opening and first and second strap members extending from opposite ends of said panel member, said first member having a rigid loop on one end remote from the panel, the second strap member having mating engagement fabric portions thereon whereby the second strap may be passed through said rigid loop of the first member, tightened into a water-tight seal on the limb and engaged upon itself with the mating engagement fabric, a rigidifying panel corresponding generally to said intermediate panel to support the wall portion of the tubular member to which said intermediate portion is fastened and fastening means cooperating with said rigidifying panel and intermediate panel to fix the wall portion of the tubular member thereto.

2. A limb protective covering as claimed in claim 1 wherein the tubular plastic member is made of polyethylene.

3. A limb protective covering as claimed in claim 1 wherein said tubular member has a foot receiving member integral therewith.

4. A limb protective covering as claimed in claim 1 wherein said tubular member has a hand receiving member integral therewith.

5. A limb protective covering as claimed in claim 1 or 2 or 3 or 4, wherein the intermediate panel of the closure member is fixed to said tubular member spaced from said open end.

6. A limb protective covering as claimed in claim 1 or 2 or 3 or 4, wherein the intermediate panel of said closure member is fixed to said tubular member adjacent the said open end and a loop is provided adjacent said open end on said tubular member spaced from said intermediate panel for receiving at least one of the ends of said closure member.

7. A limb protective covering as claimed in claim 1 or 2 or 3 or 4, wherein the rigidifying panel is a plastic impregnated fabric.

8. A limb protective device as claimed in claim 1 or 2 or 3 or 4 wherein the fastening means is stitching passing through both panels and the tubular sleeve sandwiched between.

9. A limb protective device as claimed in claim 1 or 2 or 3 or 4 wherein the rigidifying means and fastening means is a double-sided adhesive tape.

* * * * *